(12) United States Patent
Haggstrom et al.

(10) Patent No.: US 7,569,742 B2
(45) Date of Patent: Aug. 4, 2009

(54) SELF CONTAINED WOUND DRESSING WITH MICROPUMP

(75) Inventors: Kurt Haggstrom, Huntington Beach, CA (US); Alain Tranchemontagne, Warwick, RI (US); Loredana Jinga, N. Attleboro, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 109 days.

(21) Appl. No.: 11/517,210

(22) Filed: Sep. 6, 2006

(65) Prior Publication Data

US 2007/0078366 A1 Apr. 5, 2007

Related U.S. Application Data

(60) Provisional application No. 60/714,812, filed on Sep. 6, 2005.

(51) Int. Cl.
*A61F 13/00* (2006.01)
*A61M 1/00* (2006.01)
*A61M 27/00* (2006.01)

(52) U.S. Cl. .............. 602/53; 602/42; 602/43; 602/54; 602/41; 604/304; 604/305; 604/315; 604/543; 128/888

(58) Field of Classification Search ............. 128/888; 206/288, 289, 313, 315; 602/2, 41–43, 53–54; 424/443–449; 604/304, 305, 307–308, 313, 604/315, 543, 521, 48, 500, 503, 505, 176, 604/289–290

See application file for complete search history.

(56) References Cited

U.S. PATENT DOCUMENTS 4,710,165 A 12/1987 McNeil et al.
4,969,880 A 11/1990 Zamierowski
5,100,396 A 3/1992 Zamierowski
5,106,629 A 4/1992 Cartmell et al.
5,141,503 A 8/1992 Sewell, Jr.
5,176,663 A 1/1993 Svedman et al.
5,261,893 A 11/1993 Zamierowski
5,527,293 A 6/1996 Zamierowski
5,549,584 A 8/1996 Gross
5,636,643 A 6/1997 Argenta et al.
5,645,081 A 7/1997 Argenta et al.
5,678,564 A 10/1997 Lawrence et al.
5,701,917 A 12/1997 Khouri
5,779,657 A * 7/1998 Daneshvar ............. 602/60

(Continued)

FOREIGN PATENT DOCUMENTS

EP 0853950 A1 7/1998

(Continued)

*Primary Examiner*—Patricia Bianco
*Assistant Examiner*—Tarla Patel
(74) *Attorney, Agent, or Firm*—Elizabeth A. O'Brien, Esq.

(57) ABSTRACT

A composite wound dressing apparatus promotes healing of a wound via the use of a micropump system housed within or above a wound dressing member. The micropump system includes a miniature pump that applies a subatmospheric pressure to the wound to effectively draw wound fluid or exudate away from the wound bed without the need for a cumbersome external vacuum source. Hence, the wound dressing and micropump system is portable which allows the patient mobility that is unavailable when an external vacuum source is used. The patient does not need to be constrained for any period of time while exudate is being removed from the wound.

15 Claims, 7 Drawing Sheets

U.S. PATENT DOCUMENTS

| | | | |
|---|---|---|---|
| 5,911,222 A | 6/1999 | Lawrence et al. | |
| 6,071,267 A | 6/2000 | Zamierowski | |
| 6,117,111 A | 9/2000 | Fleischmann | |
| 6,135,116 A | 10/2000 | Vogel et al. | |
| 6,142,982 A | 11/2000 | Hunt et al. | |
| 6,174,306 B1 | 1/2001 | Fleischmann | |
| 6,261,276 B1 * | 7/2001 | Reitsma | 604/319 |
| 6,345,623 B1 | 2/2002 | Heaton et al. | |
| 6,398,767 B1 | 6/2002 | Fleischmann | |
| 6,458,109 B1 | 10/2002 | Henley et al. | |
| 6,488,643 B1 | 12/2002 | Tumey et al. | |
| 6,520,982 B1 | 2/2003 | Boynton et al. | |
| 6,553,998 B2 | 4/2003 | Heaton et al. | |
| 6,557,704 B1 | 5/2003 | Randolph | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,855,860 B2 | 2/2005 | Ruszczak et al. | |
| 6,856,821 B2 | 2/2005 | Johnson | |
| 6,936,037 B2 | 8/2005 | Bubb et al. | |
| 2001/0029956 A1 | 10/2001 | Argenta et al. | |
| 2001/0031943 A1 | 10/2001 | Urie | |
| 2001/0043943 A1 | 11/2001 | Coffey | |
| 2002/0065494 A1 | 5/2002 | Lockwood et al. | |
| 2002/0068913 A1 | 6/2002 | Fleischmann | |
| 2002/0082567 A1 | 6/2002 | Lockwood et al. | |
| 2002/0115952 A1 * | 8/2002 | Johnson et al. | 602/41 |
| 2002/0120185 A1 | 8/2002 | Johnson | |
| 2002/0143286 A1 | 10/2002 | Tumey | |
| 2002/0150720 A1 | 10/2002 | Howard et al. | |
| 2002/0161317 A1 | 10/2002 | Risk et al. | |
| 2002/0161346 A1 | 10/2002 | Lockwood et al. | |
| 2002/0183702 A1 | 12/2002 | Henley et al. | |
| 2002/0198503 A1 | 12/2002 | Risk, Jr. et al. | |
| 2002/0198504 A1 | 12/2002 | Risk, Jr. et al. | |
| 2003/0014022 A1 | 1/2003 | Lockwood et al. | |
| 2003/0040687 A1 | 2/2003 | Boynton et al. | |
| 2003/0050594 A1 | 3/2003 | Zamierowski | |
| 2003/0078532 A1 | 4/2003 | Ruszczak et al. | |
| 2003/0093041 A1 | 5/2003 | Risk, Jr. et al. | |
| 2003/0097100 A1 | 5/2003 | Watson | |
| 2003/0181824 A1 | 9/2003 | Odland | |
| 2003/0187367 A1 | 10/2003 | Odland | |
| 2003/0208149 A1 | 11/2003 | Coffey | |
| 2003/0212357 A1 | 11/2003 | Pace | |
| 2003/0212359 A1 | 11/2003 | Butler | |
| 2003/0219469 A1 | 11/2003 | Johnson et al. | |
| 2004/0006319 A1 | 1/2004 | Lina et al. | |
| 2004/0030304 A1 | 2/2004 | Hunt et al. | |
| 2004/0039415 A1 | 2/2004 | Zamierowski | |
| 2004/0054338 A1 | 3/2004 | Bybordi et al. | |
| 2004/0064111 A1 | 4/2004 | Lockwood et al. | |
| 2004/0064132 A1 | 4/2004 | Boehringer et al. | |
| 2004/0073151 A1 | 4/2004 | Weston | |
| 2004/0093026 A1 | 5/2004 | Weidenhagen et al. | |
| 2004/0127862 A1 | 7/2004 | Bubb et al. | |
| 2004/0127863 A1 | 7/2004 | Bubb et al. | |
| 2004/0167482 A1 | 8/2004 | Watson | |
| 2004/0193218 A1 | 9/2004 | Butler | |
| 2004/0241213 A1 | 12/2004 | Bray | |
| 2004/0243073 A1 | 12/2004 | Lockwood et al. | |
| 2004/0249353 A1 | 12/2004 | Risks, Jr. et al. | |
| 2004/0260230 A1 | 12/2004 | Randolph | |
| 2005/0004534 A1 | 1/2005 | Lockwood et al. | |
| 2005/0010153 A1 | 1/2005 | Lockwood et al. | |
| 2005/0020955 A1 | 1/2005 | Sanders et al. | |
| 2005/0028828 A1 | 2/2005 | Heaton et al. | |
| 2005/0070835 A1 | 3/2005 | Joshi | |
| 2005/0070858 A1 | 3/2005 | Lockwood et al. | |
| 2005/0085795 A1 | 4/2005 | Lockwood et al. | |
| 2005/0090787 A1 | 4/2005 | Risk, Jr. et al. | |
| 2005/0119737 A1 * | 6/2005 | Bene et al. | 623/4.1 |
| 2005/0131327 A1 | 6/2005 | Lockwood et al. | |
| 2005/0137539 A1 | 6/2005 | Biggie et al. | |
| 2005/0147562 A1 | 7/2005 | Hunter et al. | |
| 2005/0148913 A1 | 7/2005 | Weston | |
| 2006/0029650 A1 * | 2/2006 | Coffey | 424/443 |
| 2007/0055209 A1 * | 3/2007 | Patel et al. | 604/315 |

FOREIGN PATENT DOCUMENTS

| | | |
|---|---|---|
| EP | 1088569 A2 | 4/2001 |
| EP | 1219311 A2 | 7/2002 |
| GB | 2307180 A | 5/1997 |
| GB | 2329127 A | 3/1999 |
| GB | 2336546 A | 10/1999 |
| GB | 2344531 A | 6/2000 |
| WO | WO 93/09727 | 5/1993 |
| WO | WO 94/20041 | 9/1994 |
| WO | WO 96/05873 | 2/1996 |
| WO | WO 00/21586 | 4/2000 |
| WO | WO 03/005943 A2 | 1/2003 |
| WO | WO 03/018098 A2 | 3/2003 |
| WO | WO 03/030966 A1 | 4/2003 |
| WO | WO 03/045492 A1 | 6/2003 |
| WO | WO 03/057070 A2 | 7/2003 |
| WO | WO 03/057071 A2 | 7/2003 |
| WO | WO 03/057307 A1 | 7/2003 |
| WO | WO 03/086232 A2 | 10/2003 |
| WO | WO 03/092620 A2 | 11/2003 |
| WO | WO 03/101508 A2 | 12/2003 |
| WO | WO 2004/018020 A1 | 3/2004 |
| WO | WO 2005/009488 A2 | 2/2005 |

* cited by examiner

SELF CONTAINED WOUND DRESSING WITH MICROPUMP

CROSS-REFERENCE TO RELATED APPLICATIONS

This patent application claims priority to and the benefit of U.S. Provisional Patent Application No. 60/714,812, filed in the U.S. Patent and Trademark Office on Sep. 6, 2005.

BACKGROUND

1. Technical Field

The present disclosure relates to an apparatus for treating an open wound, and, more specifically, relates to a self contained wound dressing with a micropump system which draws wound fluids into a vacuum zone of the dressing to facilitate the wound healing process.

2. Description of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One technique has been to use negative pressure therapy, which is also known as suction or vacuum therapy. A variety of negative pressure devices have been developed to allow excess wound fluids, i.e., exudates to be removed while at the same time isolating the wound to protect the wound and, consequently, affect recovery time. Various wound dressings have been modified to promote the healing of open wounds.

Issues that continually need to be addressed when using a wound dressing include ease of use, efficiency of healing a wound, and a source of constant negative pressure. Thus, there remains a need to constantly improve negative pressure wound dressings for open wounds.

SUMMARY

In one preferred embodiment, a wound dressing apparatus includes a wound dressing member dimensioned for positioning relative to a wound bed and a micropump system. The micropump system includes a micropump for applying subatmospheric pressure to at least the wound dressing member to facilitate removal of fluid from the wound bed. The micropump is preferably mounted relative to the wound dressing member. The preferred micropump is adapted to produce subatmospheric pressure ranging between about 20 mmHg and about 500 mmHg.

The micropump system may include control means to control operation of the micropump. The micropump system may further include a pressure sensor adapted to detect pressure at a predetermined location relative to the wound dressing member, and send a corresponding signal to the control means. The control means may include a motor controller adapted to control or vary the output of the micropump in response to the pressure sensed by the pressure sensor. The micropump system may also include a power source, e.g., a battery, for actuating the micropump. The battery may be adapted for implantation within the wound dressing member or external to the wound dressing member. Rechargeable batteries are envisioned.

The preferred wound dressing member includes a lower member positionable adjacent the wound bed, an upper absorbent member positionable adjacent the lower member, and a top member. The micropump is at least partially positioned within the upper absorbent member. The top member is an adhesive member which is adapted to be secured about the wound bed or wound bed perimeter to provide a seal between the wound dressing member and tissue surrounding the wound bed. The lower member may include at least one of a medicament, an anti-infective agent, an antimicrobial, polyhexamethylene biguanide (hereinafter, "PHMB"), antibiotics, analgesics, healing factors, vitamins, growth factors, and nutrients and/or one of a microbead packing and/or absorbent foam. The upper absorbent member may comprise a material selected from the group consisting of foams, nonwoven composite fabrics, cellulose fabrics, super absorbent polymers, and combinations thereof.

The top member may include an occlusive material which may or may not be transparent. The wound dressing member includes a visual pressure indicator for indicating a level of pressure within the wound dressing member. The wound dressing member may include a saturation indicator to identify a degree of saturation of the wound dressing member. The top member includes an access door associated therewith and being selectively movable between a closed position substantially enclosing the wound dressing member and an open position permitting internal access to the wound dressing member.

In another embodiment, the wound dressing apparatus includes a wound dressing member including an absorbent member positionable relative to a wound bed and a micropump system contained within the wound dressing member. The micropump system includes a micropump for applying subatmospheric pressure to the wound bed to facilitate removal of fluid from the wound bed and an implantable or attachable power source for supplying power to the micropump. The micropump system includes control means to control operation of the micropump and a pressure sensor to detect pressure at a predetermined location relative to the wound dressing member.

BRIEF DESCRIPTION OF THE DRAWINGS

Various embodiments of the subject wound dressing are described herein with reference to the drawings wherein.

DESCRIPTION OF THE PREFERRED EMBODIMENTS

The composite wound dressing apparatus of the present disclosure promotes healing of a wound via the use of a micropump system housed within a wound dressing. The micropump system includes a miniature pump that applies a subatmospheric pressure to the wound to effectively draw wound fluid or exudate away from the wound bed without the need for an external vacuum source. Hence, the wound dressing apparatus in the form of wound dressing and micropump system is portable which allows the patient mobility that is unavailable when an external vacuum source is used. The patient does not need to be restricted for any period of time while exudate is being removed from the wound.

Figure 1:
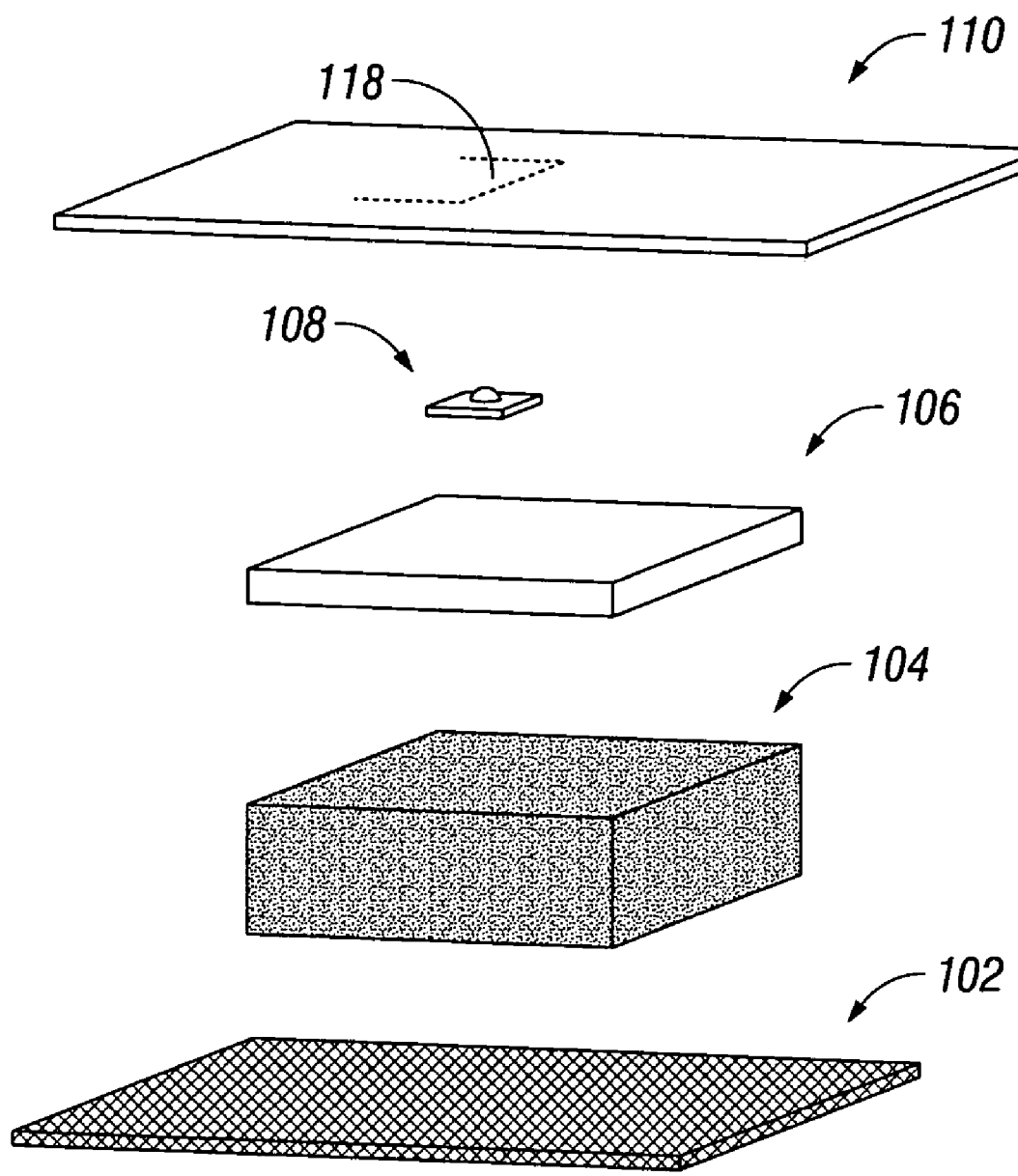
FIG. 1 is a perspective view of a self contained wound dressing and micropump system in accordance with the principles of the present disclosure.
Figure 2:
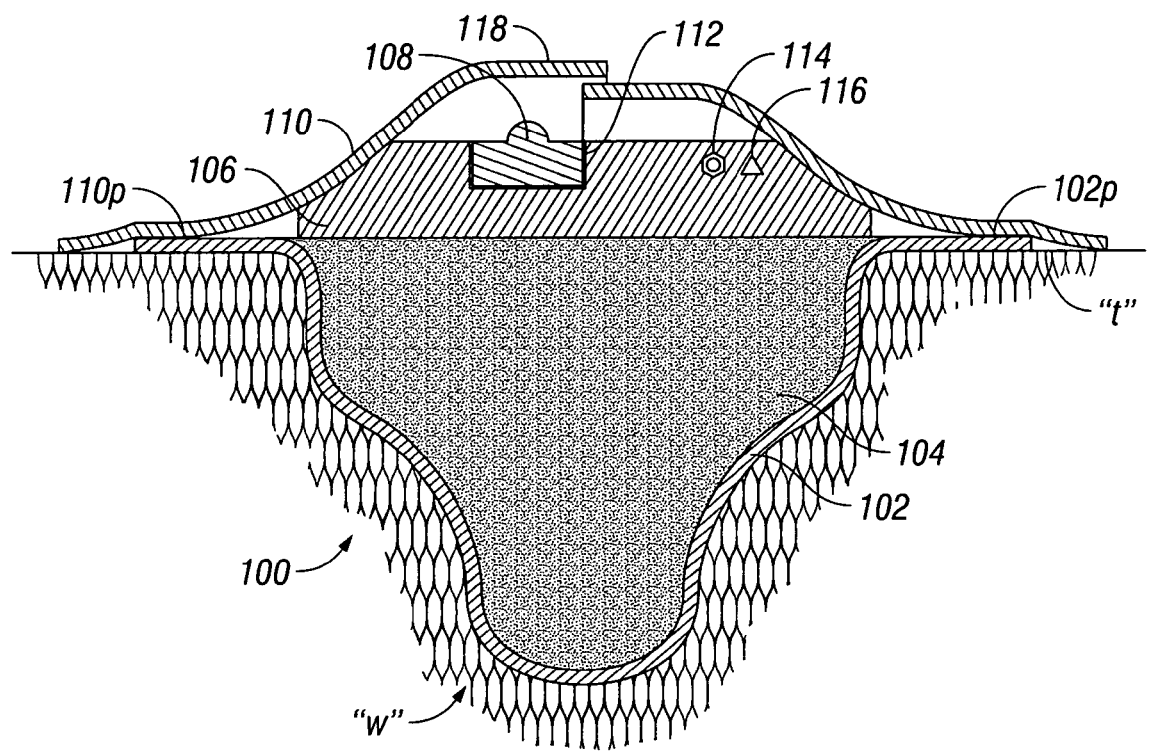
FIG. 2 is a side cross-sectional view illustrating the wound dressing on a wound bed and in a normal expanded condition in the absence of a vacuum.

Referring now to FIGS. 1 and 2, the composite wound dressing apparatus 10 in accordance with a preferred embodiment of the present disclosure is illustrated in the form of a wound dressing 100 with multiple layers arranged in juxtaposed or superposed relation. The multiple layers include, but are not limited to a base, or lower layer 102, a packing layer 104, an absorbent layer 106 which houses a micropump system 108, and a occlusive adherent top layer 110.

The base layer 102 is in direct contact with the wound bed "w" and may be adherent to the tissue or non-adherent. The base layer 102 is typically porous. "Non-adherent" as used herein refers to a material that does not adhere to tissues in and around the wound bed. "Porous" as used herein refers to a material which contains numerous small perforations or pores which allow wound fluids of all kinds to pass through the material to the dressing layers above. The passage of wound fluid through the non-adherent material is preferably unidirectional such that wound exudate does not flow back to the wound bed. This direction flow feature could be in the form of directional apertures imparted into the material layer, a lamination of materials of different absorption to the base layer 102 or specific material selection that encourages directional flow. Bidirectional flow materials are also contemplated for base layer 102 to permit infusion of fluids medicants into the wound. Exemplary materials used as the base layer 102 include a contact layer sold under the trademark XEROFLO™ by Kendall Corp, a division of TycoHealthcare.

In addition, agents such as hydrogels and medicaments could be bonded or coated to the base layer 102 to reduce bioburden in the wound, promote healing and reduce pain associated with dressing changes or removal. Medicaments include, for example, antimicrobial agents, growth factors, antibiotics, analgesics, debridement agents, and the like. Furthermore, when an analgesic is used, the analgesic could include a mechanism that would allow the release of that agent prior to dressing removal or change.

The layer proximal to the base layer 102 is the packing layer 104. The packing layer 104 is intended to absorb and capture wound fluid and exudates. Exemplary materials used as the packing layer 104 include the antimicrobial dressing sold under the trademark KERLIX™ by Kendall Corp., a division of TycoHealthcare. Those skilled in the art will recognize that the packing layer 104 can be formed into any suitable shape. One preferred characteristic as to shape is that the packing layer 104 is suitable to conform to a particular shape of the wound.

A further use for the packing layer 104 is to decrease the incidence of infection in the wound bed. Hence, the packing layer 104 may be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, debridement agents, healing factors such as vitamins, growth factors, nutrients and the like, as well as a simple flushing with agents such as isotonic saline solution.

The layer proximal to the packing layer 104 is the absorbent layer 106. The absorbent layer 106 of the wound dressing apparatus 10 is intended to absorb and capture wound fluid and exudates. The absorbent layer 106 also houses the micropump system 108. Preferably, the absorbent layer 106 is preformed or shaped to accept the micropump system 108. In this regard, the absorbent layer 106 may have a concavity or recess 112 to accommodate the micropump system 108. Alternatively, the absorbent layer 106 may be pliable so as to be shaped or formed to receive and/or confine the micropump system 108. Exemplary absorbent materials include foams, nonwoven composite fabrics, cellulosic fabrics, super absorbent polymers, and combinations thereof. Preferably, the absorbent layer 106 can absorb a substantial volume of exudates, e.g., up to at least 100 cubic centimeters (cc) or more of wound fluid. The absorbent layer 106 may include multiple layers.

The absorbent layer 106 also may be treated with medicaments. Medicaments include, for example, an anti-infective agent such as an antiseptic or other suitable antimicrobial or combination of antimicrobials, polyhexamethylene biguanide, antibiotics, analgesics, healing factors such as vitamins, debridement agents, growth factors, nutrients and the like, as well as a flushing agents such as isotonic saline solution.

The absorbent layer 106 may further include a pressure indicator 114 independent from the micropump system 108. The pressure indicator 114 may be mounted to, secured to, or embedded within the absorbent layer 106 or within the confines of wound dressing apparatus 10. Alternatively, the pressure indicator 114 is external to the wound dressing 100 and communicates with the interior of the wound dressing through a pressure tube or the like. The pressure indicator 114 may be in the form of the commercially available pressure sensor sold under the tradename Dynamic IP® Pressure Sensors by PCB® Piezotronics. The pressure indicator 114 may be color coded where one color on the device (e.g., red) indicates a non vacuum state and a second color (e.g., green) indicates a suitable vacuum state. The absorbent layer 106 may further include a saturation indicator 116 mounted to, or embedded within, the surface of the absorbent layer 106. The saturation indicator 116 may be a litmus paper such as but not limited to PEHANAL® and PANPEHA® which indicates to the user of the level or degree of saturation of the absorbent layer 106 with exudates and wound fluids. The saturation indicator 116 will assist the user in determining the remaining capacity of the absorbent layer 106, or if the absorbent layer 106 needs replacing. Although disclosed as being mounted to or embedded within absorbent layer 106, the saturation indicator 116 may be positioned within any component of wound dressing 100.

With reference still to FIGS. 1 and 2, the adherent top layer 110 encompasses the perimeter of the wound dressing 100 to surround the wound bed "w" to provide a seal around the perimeter of the wound bed "w". For instance, the sealing mechanism may be any adhesive bonded to a layer that surrounds the wound bed "w". The adhesive must provide acceptable adhesion to the tissue "t" surrounding the wound bed "w" skin, e.g., the periwound area, and be acceptable for use on skin without contact deterioration (for example, the adhesive should preferably be non-irritating and non-sensitizing.) The adhesive may be permeable to permit the contacted skin to breathe and transmit moisture. Additionally, the adhesive could be activated or de-activated by an external stimulus such as heat or a given fluid solution or chemical reaction. Adhesives include, for example, Ultec® Hydrocolloid Dressing or Curagel® Hydrogel by Kendall Corp., a division of Tyco Healthcare Group LP.

The adherent top layer 110 is preferably in the form of a sheet mounted proximal to the absorbent layer 106. Preferably, the top layer 110 is not bonded to the absorbent layer 106 to allow for easy replacement of the absorbent layer 106. In a preferred embodiment, the peripheral portions 110P of the top layer 110 are bonded to the periphery 1 02P of the base layer 102 and secured to the tissue "t" about the wound bed "w". It is anticipated that removable liners may also be used to protect the adhesive surface of the adherent layer 110 prior to use.

The top layer 110 is typically a flexible material, e.g., resilient or elastomeric, that seals the top of the wound dressing 100. An exemplary flexible material includes the fully or partially transparent dressing manufactured under the trademark Polyskin® II by Kendall Corp, a division of Tyco Healthcare Group LP. Polyskin® II is a transparent, semi-permeable material which permits passage of moisture from the wound site, and provides a barrier to microbes and fluid containment. In the alternative, the top layer 110 may be impermeable to moisture. The transparency of the top layer 110 provides visual indicia of the status of the wound dressing and more particularly, the status of the saturation level of the layers of the wound dressing. More specifically, the transparency of the top layer 110 permits the clinician to view the respective statuses of the pressure indicator 114 and the saturation indicator 116.

The top layer 110 may include an access door 118 to provide access to the interior of the wound dressing 100 and/or the wound bed "w". The door 118 could be a flap integrally formed with the top layer 110 or a separate component connected to the top layer 110 via a hinge or the like. The door 118 is preferably resealable to maintain the integrity of the wound dressing 100 and to provide a seal relative to the top layer 110. One suitable means for releasably sealing the door 118 includes a snap fit arrangement, tongue and groove arrangement, "zip lock®" arrangement, adhesives, VEL-CRO®, etc. The door 118 preferably provides access to the wound bed "w" to enable the clinician to monitor the status of the wound, change the absorbent layer 106, change the micropump system 108, or apply additional medical treatment to the wound such as growth factors, debriders, or other wound healing agents as needed. Once the desired procedure is completed, the access door 118 would be resealed relative to the top layer 110 to maintain the integrity of the wound dressing 100.

Figure 3:
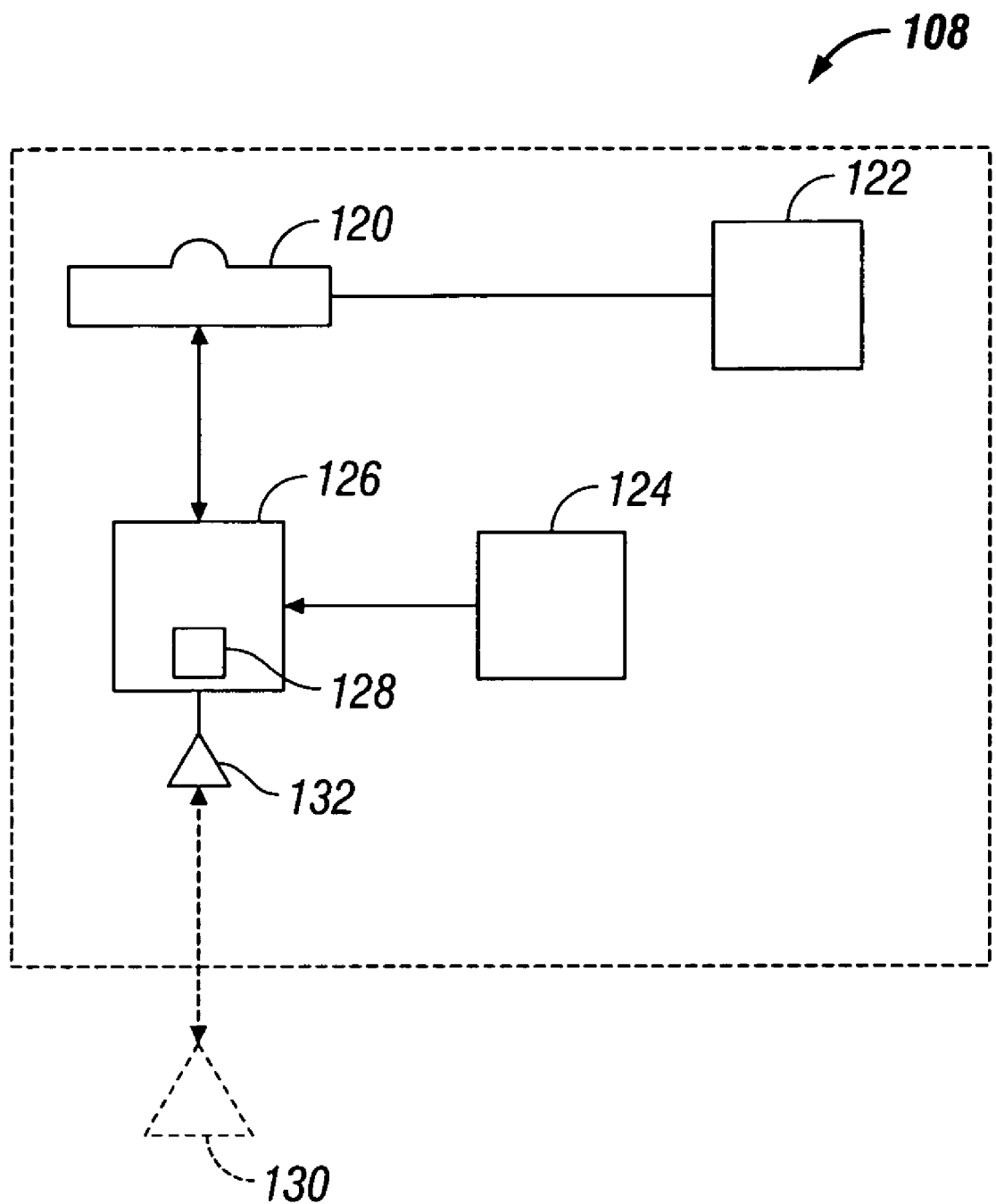
FIG. 3 is a schematic view of the micropump system.

Referring now to the schematic diagram of FIG. 3, in conjunction with FIGS. 1 and 2, the micropump system 108 will be discussed. The micropump system 108 includes a miniature pump or micropump 120 with a length ranging from about 1 to 3 inches and a relatively small diameter, preferably, no greater than about one inch. The micropump 120 may be any type of pump that is biocompatible and maintains or draws adequate and therapeutic vacuum levels. The micropump 120 may be embedded within the absorbent layer 106 or mounted to the layer 106, or alternatively associated within the confines of the wound dressing 100. "Therapeutic vacuum levels" as used herein refers to a vacuum level that draws wound fluid and exudate away from the wound bed. Preferably, the vacuum level to be achieved is in a range between about 75 mmHg and about 125 mmHg. The micropump 120 may be disposable, removable, reusable, and/or rechargeable. Typically, the micropump 120 is a pump of the diaphragmatic or peristaltic type, or the like, in which the moving part(s) draw exudate out of the wound bed into the wound dressing by creating areas or zones of decreased pressure e.g., vacuum zones with the wound dressing 100. This area of decreased pressure preferably communicates with the wound bed "w" to facilitate removal of the fluids therefrom and into the absorbent layer 106. The micropump 120 may be actuated by any means known by those skilled in the art. In a preferred embodiment of the present disclosure, the micropump 120 is a peristaltic pump. One suitable micropump is manufactured by Piab Vacuum Products in Hingham, Mass. Preferably, the peristaltic pump produces subatmospheric pressure ranging from about 20 mmHg to about 500 mmHg.

The micropump system 108 preferably includes an internal self contained battery source 122, a pressure sensor or transducer 124 to monitor pressure adjacent the micropump 120 or selected locations displaced from the micropump 120, and regulation or control means 126. The control means 126 may incorporate a motor controller/driver 128 including processing and drive circuitry to control or vary the drive voltage to the motor of the micropump 120 responsive to the pressure sensed by the pressure sensor 124. The output of the motor of the micropump 120 may be increased or decreased, or initiated or discontinued, as controlled by the control means 126. The pressure sensor 124 would also provide information to assist in detecting a leak in the wound closure apparatus 10 if the optimal subatmospheric pressure is not achieved. The regulation or control means 126 may also have an alarm such as a visual, audio or tactile sensory alarm (e.g., vibratory etc.) to indicate to the user when specific conditions have been met (e.g., the desired vacuum level or loss of vacuum).

The micropump system 108 is preferably adapted for implantation within the wound dressing 100, i.e., it is an implantable self-contained unit. The battery source 122 and control means 126 may be built into the housing of the micropump 120. The pressure sensor 124 may be mounted to the external surface of the housing of the micropump 120 or communicate through a port in the housing. The pressure sensor 124 may also be displaced from the housing of the micropump 118, e.g., embedded within the absorbent layer 106 at a location displaced from the micropump 120, and connected to the control means 126 through an electrical connection. The micropump 120 and battery 122 may be disposable or rechargeable. Preferably, the micropump system 108 is entirely disposable, e.g., after a single use, and is disposed of along with the absorbent layer 106 of the wound dressing 100. Alternatively, the micropump system 108 may be removed or disconnected from the absorbent layer 106 and reinstalled into another absorbent layer 106 for placement within the wound closure 100.

It is also envisioned that the micropump system 108 may be externally controlled via radio transmitter means. In this alternate embodiment, an external radio frequency (RF) transmitter or antenna 130 (shown in phantom on FIG. 3) may send/receive signals to a receiving transmitter 132 associated with the control means 126 to operate the control means to control functioning of the micropump system 108. One skilled in the art may readily adapt the micropump system 108 to operate via remote radio frequency (RF) means. The micropump system 108 may incorporate circuitry to communicate with a computer, e.g., a hand-held PALM device.

Figure 4:
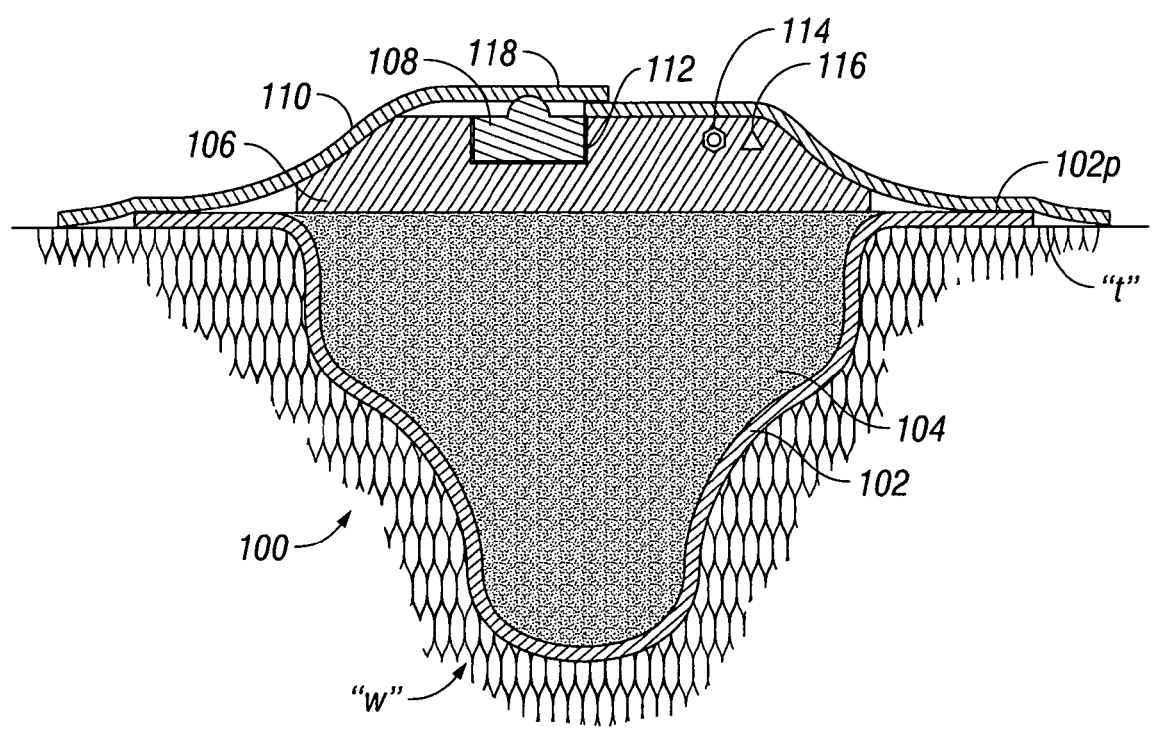
FIG. 4 is a view similar to the view of FIG. 2 illustrating the wound dressing in a contracted condition when subjected to subatmospheric pressure generated by the micropump system.

In use, the wound dressing 100 is positioned within the wound bed "w" as shown in FIG. 2. Thereafter, the micropump 120 is initiated to create a zone of subatmospheric pressure (i.e., a state of vacuum) within the wound dressing 100. The micropump 120 may be initiated via a manual switch associated with the control means 126, or may be started via the pressure sensor 124 which detects the lack of subatmospheric pressure within the wound dressing 100 and sends a corresponding signal to the control means 126. The control means 126, in turn, activates the micropump 120. As the subatmospheric pressure within the wound closure 100 increases, the top layer 110 collapses to the position depicted in FIG. 4. Once the desired level of subatmospheric pressure is achieved as detected by, e.g., the pressure sensor 124, the pressure sensor 124 sends a signal to the control means 126. The control means 126 may either terminate operation of the micropump 120 or alternatively vary the speed or output (e.g., decrease) of the micropump 120. In the vacuum state, wound fluid and exudates are drawn into the absorbent layer 106 to be collected therein. After a period of time, the wound dressing 100 may lose its vacuum state as detected by the pressure sensor 124. Visual confirmation of the loss of vacuum state may also be ascertained by viewing the vacuum indicator 114 through the top layer 110. When the loss of a desired vacuum level is achieved, the pressure sensor 124 sends a signal to the control means 126 to activate or increase the output of the micropump 120. This process may continue several times during wound healing.

Figure 5:
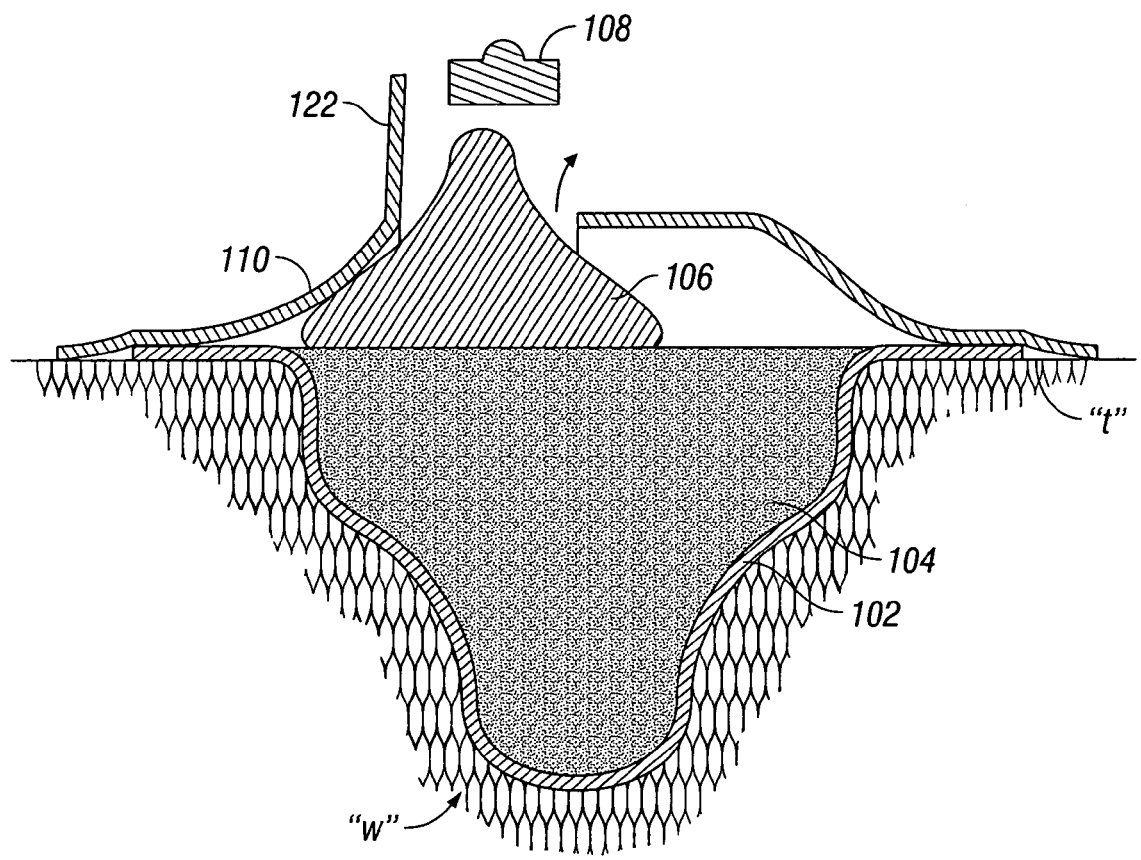
FIG. 5 is a view illustrating the access door of the wound dressing in an open condition to permit removal of the absorbent layer and/or micropump system.

Once the absorbent layer 106 is fully saturated as detected by viewing the saturation indicator 116 through the top layer 110, the access door 118 may be opened as shown in FIG. 5. The absorbent layer 106 and the micropump system 108 may be removed through the door. As discussed, a new absorbent layer 106 and/or new micropump system 108 subsequently may be introduced through the door 118 and installed within the wound dressing 100.

Figure 6:
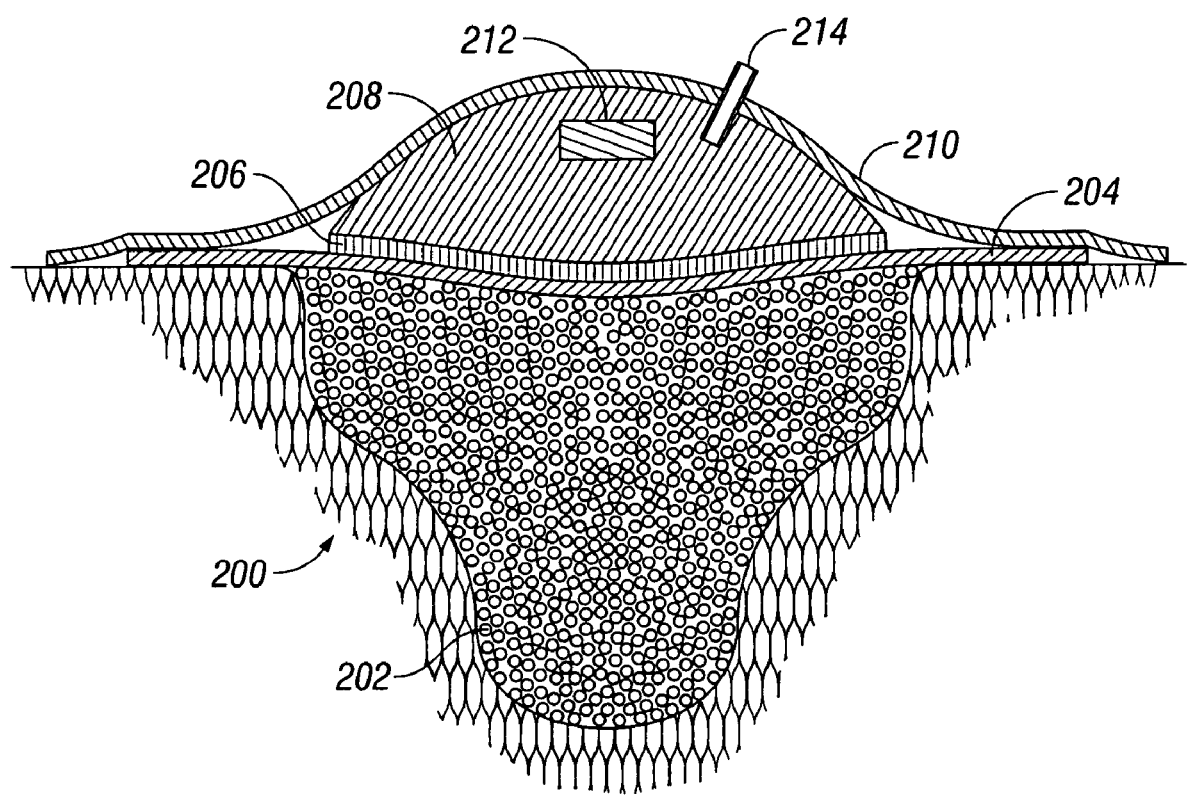
FIG. 6 is a side cross-sectional view of another embodiment of the self contained wound dressing and micropump system of the present disclosure.

FIG. 6 illustrates an alternate embodiment of the present disclosure. In accordance with this embodiment, wound dressing 200 includes a bead packing 202, contact layer 204, capillary layer 206, packing layer 208 and occlusive layer 210. Bead packing 202 may incorporate a plurality of antimicrobial beads, beads with growth factors, medicaments, antibiotics, analgesics, and healing factors such as vitamins, growth factors, nutrients and the like. These beads are preferably non-adherent and may be bioabsorbable over a predetermined period of time. Alternatively, the beads may be non-absorbable. The beads may be injectable into the wound site. Multiple applications of the beads are also contemplated.

Alternatively, contact layer 204 may be similar to the base layer 102 discussed hereinabove and is preferably porous. Capillary layer 206 includes a plurality of capillary fibers defining microchannels that permit controlled directional flow of a liquid, e.g., to permit drainage of the exudates from the wound. These channels formed in sheets, films, or tubes may be uniform in dimension or random and extend along the length of the layer. The microchannels desirably permit fluid flow in one direction, i.e., away from the wound for wound drainage, for example, similar to dialysis filters. Packing layer 208 and micropump 212 are substantially similar to their counterparts discussed hereinabove. Occlusive layer 210 may comprise a silicon or hydrogel material that can be adherent on the skin contact side and non-adherent to the outer side, and is preferably adherent in moist/oily environments. The occlusive layer 210 may also be a film forming liquid material which is dispensed from a spray mechanism for application over the dressing with the same surface characteristics described above. Wound dressing 200 may further incorporate a supplemental port 214 for connection to an external drainage canister or such as a drainage bag.

Figure 7:
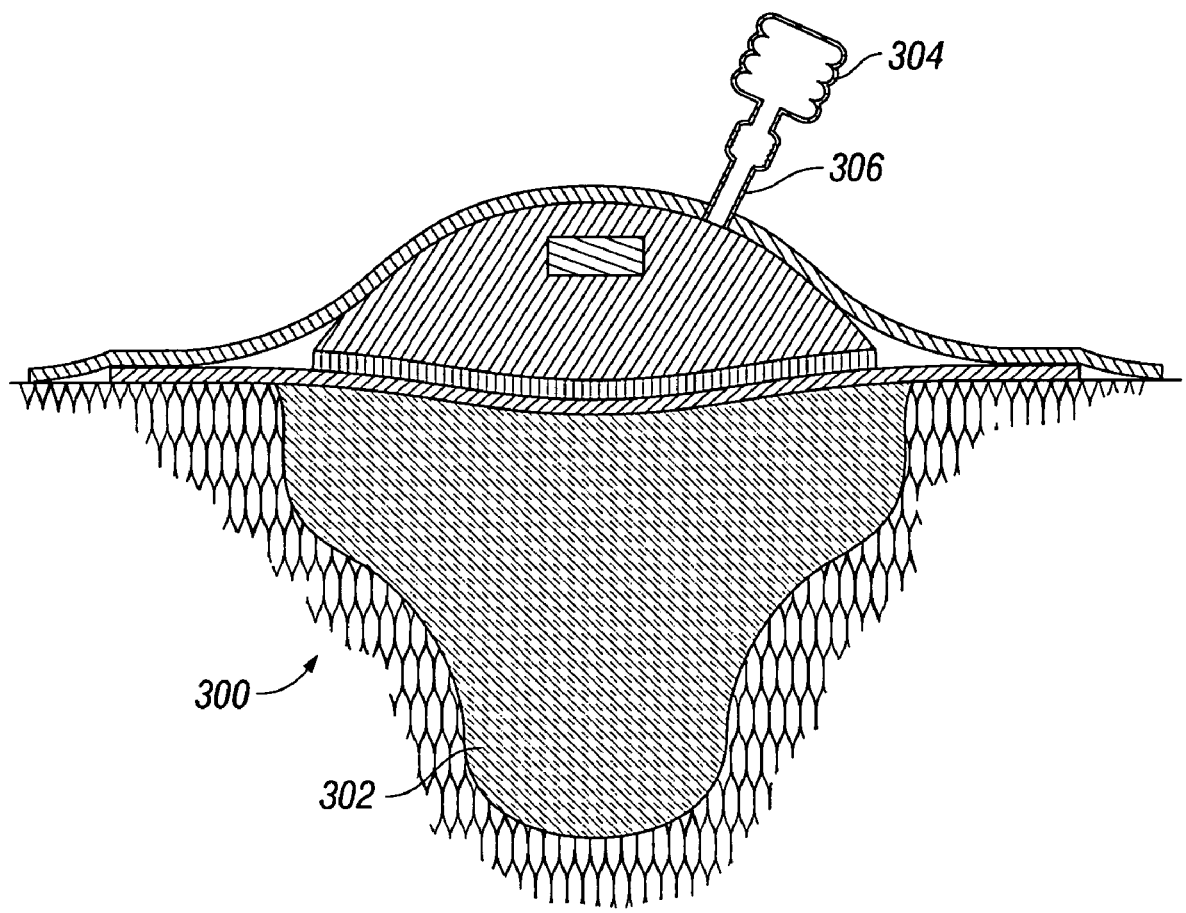
FIG. 7 is a side cross-sectional view of yet another embodiment of the self contained wound dressing and micropump system of the present disclosure.

FIG. 7 illustrates an alternate wound dressing 300 which incorporates biocompatible foam 302 in lieu of the bead layer. The foam 302 may be a resilient, liquid absorbent, porous, polymer-based foam. The foam 302 may be a dispensable liquid which at least partially solidifies to a crystal-like arrangement defining hollow tubes to allow exudates drainage. The foam 302 is dispensed within the wound bed and is potentially collapsible to expel air from the foam channels. The foam 302 may be an expandable hydrophilic foam which is capable of absorbing fluid from a wound and maintain the wound bed moist. The hollow tubes or voids defined by the foam 302 also provide a means to conduct electricity, heat, cold, and ultrasound. The hollow tubes or voids also provide a bioactive scaffold for tissue growth. Wound dressing 300 further includes an accordion style bag or canister 304 connected to the interior of dressing 300 through port 306. Canister 304 may be compressed to impart energy to the wound exudates to drain the fluid into the bag. One suitable system is disclosed in commonly assigned U.S. Pat. No. 5,549,584 to Gross, the entire contents of which are hereby incorporated herein by reference. A one-way valve may be incorporated into the port leading to canister 304 if desired.

It is further contemplated that the wound dressing apparatus may incorporate external means or applications to stimulate tissue growth and/or healing. For example, an ultrasonic transducer may be incorporated into the wound dressing apparatus to impart mechanical energy for the treatment of the tissue such as, for instance, directing thermal or vibratory energy on the wound area and/or introducing various drugs into the human body through the skin. Other sensor types are also contemplated for incorporation into the wound dressing apparatus including oxygen, chemical, microbial, perfusion and/or temperature sensors. The detection of oxygen adjacent the wound area would assist the clinician in determining the status of wound healing. The presence of an elevated temperature may be indicative of an infection.

While the disclosure has been illustrated and described, it is not intended to be limited to the details shown, since various modifications and substitutions can be made without departing in any way from the spirit of the present disclosure. For example, it is envisioned the subject matter of the commonly assigned patent application filed concurrently herewith under Express Mail Certificate No. EL 985194499 US, and which claims priority to provisional application No. 60/714,805, filed on Sep. 7, 2006, and the subject matter of the commonly assigned patent application filed concurrently herewith under Express Mail Certificate No. EL 985194539 US, and which claims priority to provisional application No. 60/714,912, filed on Sep. 7, 2006, (the entire contents of each application being incorporated herein) may be incorporated into the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A wound dressing apparatus, which comprises:
    a wound dressing member including a cover member dimensioned for positioning over a wound bed; and
    a micropump system including:
        a micropump for applying subatmospheric pressure to at least the wound dressing member to facilitate removal of fluid from the wound bed, the micropump being disposed beneath the cover member adjacent the wound bed;

a pressure sensor adapted to detect pressure at a predetermined location relative to a wound dressing member, and send a corresponding signal to the control means said the control means include a motor controller adapted to control or vary the output of the micropump in response to the pressure sensed by the pressure sensor.

2. The wound dressing apparatus according to claim 1 wherein the micropump is adapted to produce subatmospheric pressure ranging between about 20 mmHg and about 500 mmHg.

3. The wound dressing apparatus according to claim 1 wherein the micropump system includes a battery for actuating the micropump, the battery adapted for implantation within the wound dressing member.

4. The wound dressing apparatus according to claim 1 wherein the wound dressing member includes a lower member positionable adjacent the wound bed, an upper absorbent member positionable adjacent the lower member, and a top member.

5. The wound dressing apparatus according to claim 4 wherein the micropump is at least partially positioned within the upper absorbent member.

6. The wound dressing apparatus according to claim 5 wherein the top member is an adhesive member, the adhesive member adapted to be secured about the wound bed to provide a seal between the wound dressing member and tissue surrounding the wound bed.

7. The wound dressing apparatus according to claim 4 wherein the lower member includes at least one of a medicament, an anti-infective agent, an antimicrobial, polyhexamethylene biguanide (hereinafter, "PHMB"), antibiotics, debridement agents, analgesics, healing factors, vitamins, growth factors, and nutrients.

8. The wound dressing apparatus according to claim 4 wherein the upper absorbent member comprises a material selected from the group consisting of foams, nonwoven composite fabrics, cellulosic fabrics, super absorbent polymers, and combinations thereof.

9. The wound dressing apparatus according to claim 8 wherein the upper absorbent member includes at least one of a medicament, an anti-infective agent, an antimicrobial, polyhexamethylene biguanide (hereinafter, "PHMB"), antibiotics, analgesics, healing factors, vitamins, growth factors and nutrients.

10. The wound dressing apparatus according to claim 4 wherein the top member comprises a transparent material.

11. The wound dressing apparatus according to claim 10 wherein the wound dressing member includes a pressure indicator for indicating a level of pressure within the wound dressing member.

12. The wound dressing apparatus according to claim 10 wherein the wound dressing member includes a saturation indicator to identify a degree of saturation of the wound dressing member.

13. The wound dressing apparatus according to claim 4 wherein the top member includes an access door associated therewith and being selectively movable between a closed position substantially enclosing the wound dressing member and an open position permitting internal access to the wound dressing member.

14. A wound dressing apparatus, which comprises:
a wound dressing member including an absorbent member positionable relative to a wound bed; and
a micropump system contained within or adjacent to the wound dressing member, the micropump system including:
a micropump for applying subatmospheric pressure to the wound bed to facilitate removal of fluid from the wound bed, the micropump being at least partially encapsulated within the absorbent member;
a pressure sensor to detect pressure at a predetermined location relative to the wound dressing member and a control means includes a motor controller adapted to control or vary the output of the micropump in response to the pressure sensed by the pressure sensor.

15. The wound dressing apparatus according to claim 14 wherein the micropump system includes a battery for supplying power to the micropump.

* * * * *

UNITED STATES PATENT AND TRADEMARK OFFICE
CERTIFICATE OF CORRECTION

PATENT NO.       : 7,569,742 B2                                              Page 1 of 1
APPLICATION NO.  : 11/517210
DATED            : August 4, 2009
INVENTOR(S)      : Kurt Haggstrom et al.

It is certified that error appears in the above-identified patent and that said Letters Patent is hereby corrected as shown below:

On the Title page Item (65) Related U.S. Application Data

(65) "Provisional application No. 60/714,812, filed on Sep. 6, 2005" should be

--Provisional application No. 60/714,812, filed on September 7, 2005--.

Signed and Sealed this

Thirteenth Day of November, 2012

David J. Kappos
*Director of the United States Patent and Trademark Office*